(12) United States Patent
Alraheem

(10) Patent No.: US 12,636,195 B1
(45) Date of Patent: May 26, 2026

(54) DOME BANDAGE

(71) Applicant: Hakeem Alraheem, Turlock, CA (US)

(72) Inventor: Hakeem Alraheem, Turlock, CA (US)

( * ) Notice: Subject to any disclaimer, the term of this patent is extended or adjusted under 35 U.S.C. 154(b) by 0 days.

(21) Appl. No.: 18/899,525

(22) Filed: Sep. 27, 2024

Related U.S. Application Data

(63) Continuation-in-part of application No. 17/179,169, filed on Feb. 18, 2021, now abandoned.

(60) Provisional application No. 62/990,289, filed on Mar. 16, 2020.

(51) Int. Cl.
*A61F 13/01* (2024.01)
*A61F 13/00* (2024.01)

(52) U.S. Cl.
CPC .. *A61F 13/01021* (2024.01); *A61F 13/01017* (2024.01); *A61F 13/01034* (2024.01); *A61F 2013/00165* (2013.01); *A61F 2013/00182* (2013.01); *A61F 2013/00217* (2013.01); *A61F 2013/00251* (2013.01); *A61F 2013/00272* (2013.01)

(58) Field of Classification Search
CPC ...... A61F 2013/00165; A61F 13/00059; A61F 13/00021; A61F 13/00029; A61F 15/008; A61F 5/3761; A61F 13/01021; A61F 13/01034; A61M 2025/0246; A61M 5/52; A61M 25/02

See application file for complete search history.

(56) References Cited

U.S. PATENT DOCUMENTS

| | | | | |
|---|---|---|---|---|
| 6,500,154 B1 * | 12/2002 | Hakky | ................. | A61M 25/02 |
| | | | | 604/179 |
| 2008/0243082 A1 * | 10/2008 | Goodman | ............. | A61M 25/02 |
| | | | | 604/180 |
| 2018/0289556 A1 * | 10/2018 | Levy | .................. | A61F 13/0233 |

* cited by examiner

*Primary Examiner* — Ophelia A Hawthorne
(74) *Attorney, Agent, or Firm* — John Rizvi; John Rizvi, P.A.—The Patent Professor®

(57) ABSTRACT

A reusable bandage apparatus for covering a wound is disclosed. The reusable bandage apparatus comprises a dome configured to cover and protect a skin wound. The reusable bandage apparatus also comprises a flange extending around the base of the dome, wherein the flange is configured to rest on non-injured skin surrounding the skin wound. The reusable bandage apparatus further comprises a plurality of protrusions located on the underside of the flange, wherein the plurality of protrusions is configured to create a gap between the flange and the non-injured skin.

20 Claims, 5 Drawing Sheets

100

202

104

106

DOME BANDAGE

CROSS-REFERENCE TO RELATED APPLICATIONS

This application is a Continuation-in-part under 35 U.S.C. § 120 of the U.S. patent application Ser. No. 17/179,169 filed on Feb. 18, 2021, which claims the benefit of the U.S. Provisional Patent Application Ser. No. 62/990,289 filed on Mar. 16, 2020, both of which are incorporated by reference herein in their entirety.

FIELD OF THE INVENTION

The present invention relates to bandage devices, and more particularly to reusable bandage devices having a dome-shaped covering to protect a wound area.

BACKGROUND OF THE INVENTION

Removing bandage padding is very painful if conventional skin wound bandage padding adhesive materials are applied on top of an injured skin. The bandage padding absorbs excess blood and platelets in the wound and eventually fuses and hardens the scab to the padding. When lifting the bandage padding after the blood had dried, and hardened on the affected wound, the injured skin will rupture; disrupt the scab causing pain and will require the scab wound to re-harden for repeated proper healing. The adhesive bandage materials used to append the bandage around the wound, creates an air locked seal between the skin and the chemical bonding materials clogs skin pores. When lifting the appended adhesive bandage materials from skin tissue; attached hair follicles will be pulled from skin causing pain when the said adhesive is removed.

Conventional skin wound bandage padding material applied on top of an injured skin, does not offer impact protection for wounds if padding creases or crushes on impact. If physical contact is made by an external object on conventional skin wound bandage padding, the said bandage padding materials will crease or crush an enclosed skin wound, causing pain and scab damage.

Inspecting and viewing skin wounds from a conventional skin wound bandage, requires the removal of the bandage padding material applied on top of the injured skin. As previously stated, removing the padding for inspecting and viewing the skin wound, will be very painful to the injured victim.

Conventional skin wound bandage padding material applied on top of the injured skin, does not offer visual indication as to when the said bandage should be temporarily removed for inspections, and or permanently removed for proper healing.

Conventional skin wound bandage padding material applied on top of the injured skin, was never intended be viewed, unless the padding from the wound, was removed for wound viewing. As previously stated, removing the padding for inspecting and viewing the skin wound, will be very painful to the injured victim.

Conventional skin wound bandage padding material applied on top of the injured skin, blocks the wound from having direct and indirect exposures to natural light and air; and skin adhesive bonding materials clogs skin pores, and will also block and prevent uninjured natural skin from natural skin gas exchanges.

Conventional skin wound bandage padding material applied on top of the injured and uninjured skin, are indicative to blocking skin from having exposures to air, and sunlight. Such skin blocking wound padding material, also prevents natural skin from natural skin gas exchanges, and the said padding will cause the skin to become pale from lack of air and sunlight. For proper skin health, the skin must have proper air and sunlight exposure.

Conventional skin wound bandages are not reusable, and skin wound bandages are improperly discarded, padding with blood or wound secretion materials, can become bio-hazard risk.

Through the succeeding years, variants were presented in an attempt to alleviate these problems listed. There were many variations, including the use of dome or cup-shaped covers secured by separate adhesive means as shown in Lesher, (U.S. Pat. No. 2,632,443), Schimmel, (U.S. Pat. No. 3,334,626) and Connally, (U.S. Pat. No. 1,616,156). Other variations such as that described in Reinitz, (U.S. Pat. No. 1,956,695) involved transparent impermeable device secured by an adhesive strip for collecting secretions while Barbieri (U.S. Pat. No. 3,874,387) disclosed a similar device which included fluid valves. Stumpf, (U.S. Pat. No. 2,785, 677) and Schaar, (U.S. Pat. No. 4,212,296) each disclose a protective device having a domed portion, but each suffered from a allowing wound natural flowing air effect whereby bacteria will grow instead of healing, and the wound will become infected. Fryslie, (U.S. Pat. No. 4,667,666) is a disposable device with foraminous vents on top of protective layer used to cover the wound, however such options in using foraminous vents will weakens the structure and makes it easy to crack or break on external impact. Foraminous vents, allow liquids, dust and debris to pass through the top of the said device and thus, will not aid in blocking contaminates from entering directly making contact with wound, from top of the said device vents. Also the said device flange uses a bonding adhesive compound to stick to the skin, thus removing the device; hair follicles will be pulled from the roots causing pain, and since the device was not designed for real-time wound viewing or observation without removing the said device, the user must remove the device to inspect the wound. Lemelson, (U.S. Pat. No. 4,285,338) discloses touching the wound with absorbent materials and enclosed with an opaque hard cover and held by adhesive tape. Furthermore, none of the prior devices were able hold on the skin without an adhesive compounds and such compounds blocks the skin and wound from having proper natural skin gas exchanges, airflow protection, and sunlight.

Additionally, Kennedy (U. S. Patent Application No. 2016/0100985) discloses an eye patch device, where the shape of the eye patch device is limited to the face and eyes. The flange of the eye patch device is flexible and does not offer ultraviolet (UV) protection. Further, Levy (U. S. Patent Application No. 2018/0289556) discloses a device with vents located on the top of the device, but these vents weaken the structural integrity of the device, making the device prone to shattering or breaking upon impact. Although Levy's device supports the use of UV-resistant materials to protect the device itself, it does not prevent UV rays from entering the device and exposing the wound to UV light. This is a critical shortcoming, as UV exposure can be harmful to healing wounds.

As previously stated, adhesive compounds on skin, clogs skin pores and prevents healthy or injured skin from natural skin gas exchanges, and the said adhesive compound leaves a residue on the skin, and film substances sticks to hair follicles, collects debris, oils and unsanitary partials from external sources. Furthermore, not one of the mentioned devices collectively or individually resolve problems mentioned with regards to adhesive bonding materials. Neither of the mentioned devices addresses adjustability of their devices in establishing optimal comfort while on extremities, and adhesiveness weakens or will eventually fail to adhere to the skin if removed and readjusted on the skin. Neither of the mentioned devices addressed photosensitive skin wounds protection nor supporting ultraviolet resistant materials. Neither devices are reusable nor must be discarded after use. Lastly, neither the mentioned devices addressed how long the device are to remain on the skin nor the conditions of which to replace, or permanently remove the said device from use.

The present invention solution is a reusable synthetic hard ultraviolet resistant clear transparent dome cover, placed over the skin wound without any part of the said dome device touching the skin wound, and without the risk of pain caused by the said dome device; and the said device is held on the skin by porous natural skin gas exchanges non-adhesive ribbon tape to be fitted and adjustably positioned on to the uninjured part of the human anatomy, and the said device remains on the body until the wound heals, without tape adhesives or bonding materials to clogs skin pores.

Conventional skin wound bandage and current patent devices padding material are applied on top of the injured skin will touch and adhere to the wound. The benefits in comparison with the skin wound enclosed by the said ultraviolet resistant synthetic hard clear transparent dome cover device, the said device hollow area will not allow contact to the wound and is indicative in circumventing the problems associated to materials touching the wound.

Conventional skin wound bandage and current patent devices padding material are applied on top of the injured skin prevents the wound from being viewable. The benefit in comparison with the skin wound enclosed by the said ultraviolet resistant synthetic hard clear transparent dome cover device, the skin wound is always ocularly viewable and clearly visible without needing to remove the said device until the wound is completely healed.

Conventional skin wound bandage and current patent devices padding material are applied on top of the injured skin wound covered, and natural exchanges of skin gases are blocked. The benefit in comparison with the skin wound enclosed by the said ultraviolet resistant synthetic hard clear transparent dome cover device is not hermetic, and yet the device maintains moister while natural skin gas exchanges inside the device, and from the flange.

Conventional skin wound bandages and current patent devices requires disposal of used bandages and may be hazardous if materials not properly treated or disposed. The benefit in comparison with the skin wound enclosed by the said ultraviolet resistant synthetic hard clear transparent dome cover device does not touch the wound, and the said device is durable for repeated reuse after aseptic, and or sterilization methods.

Conventional skin wound devices and current patent devices require skin pore clogging materials to hold on to the skin. The benefits in comparison with the skin wound enclosed by the said ultraviolet resistant synthetic hard clear transparent dome cover device does not support bonding adhesives nor requires adhesive tape. The slits on the flange supports the porous natural skin gas exchanges non-adhesive ribbon tape to securely fasten to the said device, and securely fasten to the uninjured part of the human anatomy.

Conventional skin wound devices and current patent devices require adhesive bonds or adhesive tape to be bonded to the skin. Once the said adhesive bonds are affixed on the skin, the device is not adjustable, and upon any relocation of the said device, the adhesive materials bond weakens. The benefits in comparison with the skin wound enclosed by the said ultraviolet resistant synthetic hard clear transparent dome cover device, the non-adhesive tape straps are adjustable to suit the comfort of the injured person and can be adjusted any number of times without losing its effectiveness to append on the skin.

Conventional skin wound devices and current patent devices require adhesive bonds or adhesive tape to be bonded to the skin. Once the said adhesive bonds are affixed on the skin, the sticky film attaches to debris, skin oils, where bacteria and fungus spores can accumulate and grow. The benefits in comparison with the skin wound enclosed by the said ultraviolet resistant synthetic hard clear transparent dome cover device, non-adhesive tape straps are not held on the skin by sticky film adhesives, therefore it is easy to wipe clean any oils or unsanitary debris from non-adhesive tape.

Conventional skin wound devices and current patent devices does not offer ultraviolet resistant materials nor protect photosensitive skin wounds from sunlight ultraviolet rays. The benefits in comparison with the skin wound enclosed by the said ultraviolet resistant synthetic hard clear transparent dome cover device is ultraviolet resistant and protects photosensitive skin wounds from sunlight ultraviolet rays.

SUMMARY OF THE INVENTION

According to an implementation of the present disclosure, there is provided a reusable bandage device. The reusable bandage apparatus comprises a dome configured to cover and protect a skin wound and a flange extending around a base of the dome, wherein the flange is configured to rest on non-injured skin surrounding the skin wound. The reusable bandage apparatus also comprises a plurality of protrusions located on the underside of the flange, wherein the plurality of protrusions is configured to create a gap between the flange and the non-injured skin.

In an aspect, the dome may be a translucent, water-impermeable, optically transparent, and ultraviolet-resistant synthetic material.

In an aspect, each of the plurality of protrusions may be a raised structure under the flange.

In an aspect, each of the plurality of protrusions may be configured to allow airflow to the skin wound while the dome is securely positioned over the skin wound.

In an aspect, a shape of the dome may vary from circular to elliptical.

In an aspect, a shape of the dome may vary from square to oblong.

In an aspect, the dome may be configured to block ultraviolet light and to protect the skin wound from sun exposure.

In an aspect, the dome may comprise a transparent material that enables visual inspection of the skin wound without removing the reusable bandage device.

In an aspect, the reusable bandage apparatus may further comprise slits through the flange for the insertion of a ribbon tape, wherein the ribbon tape may be configured to secure the reusable bandage apparatus around an extremity without adhesive, and wherein the plurality of protrusions may be configured to maintain airflow for the skin wound independent of tightness of the fit of the ribbon tape.

In an aspect, an interior part of the dome may be structured to enclose the skin wound without contacting a surface of the skin wound.

In an aspect, the dome may comprise a solid and unperforated top surface to block ultraviolet (UV) light.

In an aspect, a size and a shape of each protrusion may be determined based on a size of the wound area and a healing stage.

According to another implementation of the present disclosure, there is provided a wound care device. The wound care apparatus comprises a reusable dome configured to cover a wound area, wherein the dome is constructed from an optically transparent, ultraviolet-resistant material. The wound care apparatus also comprises a flange formed with the base of the dome, the flange extending outwardly from the dome to engage with a portion of uninjured skin surrounding the wound area. The wound care apparatus further comprises a plurality of air channels embedded within the flange, wherein the plurality of air channels is configured to direct airflow to the dome.

In an aspect, the plurality of air channels within the flange may be arranged in a geometric pattern based on a size of the wound area.

In an aspect, a height of each of the plurality of air channels may be modified based on the wound area and the surrounding uninjured skin.

In an aspect, at least one of the plurality of air channels may comprise one or more filter elements to prevent entry of contaminants to the wound area.

In an aspect, the dome may be provided with an adjustable securing mechanism comprising one or more attachment elements coupled to the flange for securing the wound care apparatus to surrounding body parts without direct adhesive contact.

In an aspect, the securing mechanism may comprise a non-adhesive and elastic strap threaded through slits in the flange for adjustable and secure attachment around the wound area.

In an aspect, each of the plurality of air channels may be detachable from the flange.

In an aspect, wherein a size and a shape of each air channel are determined based on a size of the wound area and a healing stage.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

Figure 1:
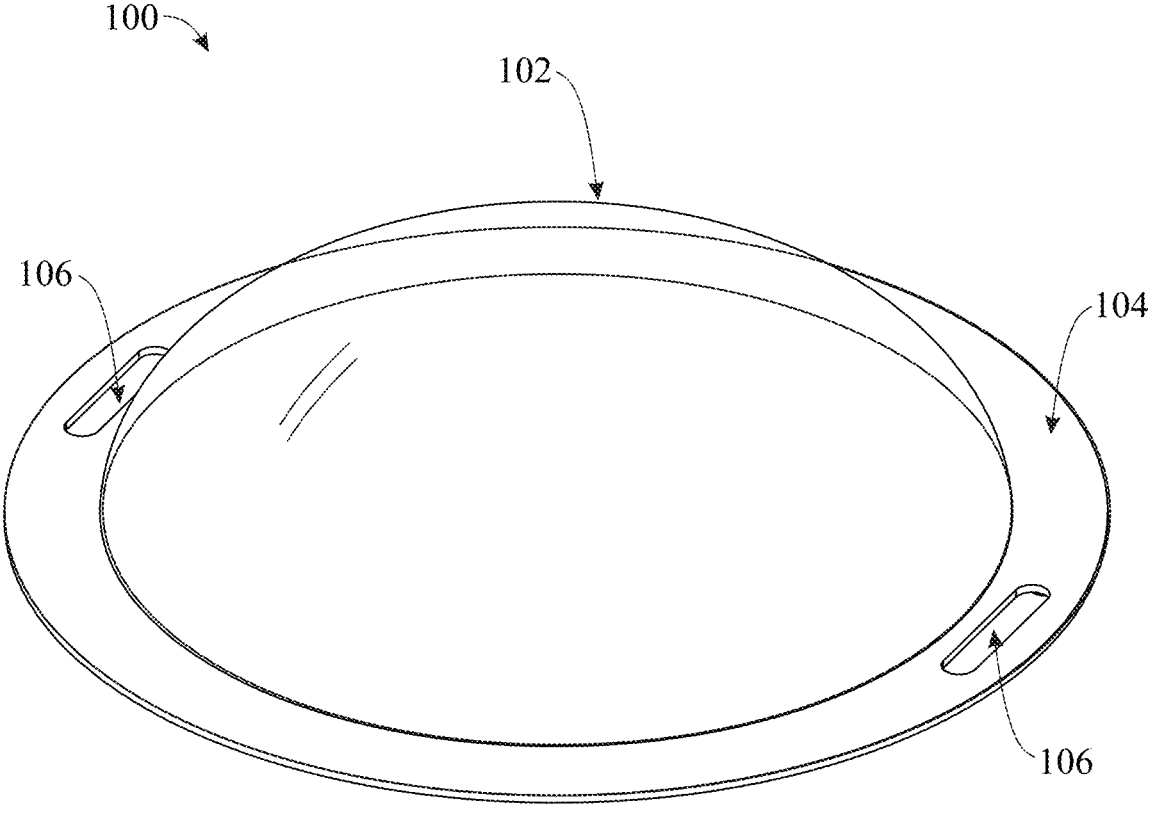
FIG. 1 illustrates a top view of the reusable bandage device in accordance with some embodiments of the present disclosure.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Unless the context requires otherwise, throughout the specification and claims which follow, the word "comprise" and variations thereof, such as, "comprises" and "comprising" are to be construed in an open, inclusive sense, that is as "including, but not limited to."

As used in this specification and the appended claims, the singular forms "a," "an," and "the" include plural referents unless the content clearly dictates otherwise. It should also be noted that the term "or" is generally employed in its broadest sense, that is as meaning "and/or" unless the content clearly dictates otherwise.

The headings and Abstract of the Disclosure provided herein are for convenience only and do not interpret the scope or meaning of the implementations.

The present invention relates to a reusable device (also known as a reusable bandage device or a wound care device), as indicated at FIG. 1, FIG. 2, FIG. 3, FIG. 4, and FIG. 5 for burns, rashes, cuts, impact injuries, abrasions, punctures, ulcers, chafed skin, sutures, tattoos, warts, blisters, and insect lesions wounds. While the reusable device is in use, the reusable device does not touch the wound, and the reusable device also acts as a physical barrier and shield to prevent external objects from making contact to the affected area. The entire reusable device is translucent clear and ultraviolet resistant synthetic material. The exterior wall allows clear and transparent ocular optical viewing, which allows real-time wound inspection and examination. Viewing a wound while covered and shielded allows viewing without removing the reusable device while the wound heals completely, and without being disturbed. The reusable device comprises ultraviolet resistant synthetic materials for withstanding sun degradation. The device's exterior wall blocks and shields against external ultraviolet light.

The flange bottom is the only part of the device that rest on the non-injured epidermis. The ultraviolet clear transparent synthetic material will allow wound observation and are clear from any materials that obstruct viewing. The flange favorably will not contour to the curvature of the extremities and; the said flange will not create a hermetic seal which supports air ventilation and while the reusable device is in use, external atmosphere is indicative to equaling the interior. Furthermore, the hard-shell integrity and strength are shatterproof, thus, protecting the wound during a collision with an external object. Natural venation and airflow is allowed from under the flange, where air and natural skin gas exchanges will naturally circulate and pass through under the flange and outside the chamber while the reusable device is appended on the uninjured epidermis.

The reusable device geometric shape vary from square to oblongness supporting wounds of a variety of sizes. In some embodiments, the reusable device geometric shape vary from circular to ellipticity supporting wounds of a variety of sizes. The reusable device is durable for cleaning with antimicrobial solvents and solutions and sterilization methods.

FIG. 1 illustrates a top view of a reusable bandage device 100 in accordance with some embodiments of the present disclosure. The reusable bandage device 100 comprises a dome 102. In some embodiments, the dome is at the center of the reusable bandage device 100. In some embodiments, the dome 102 is designed to cover and protect a wound area from external elements such as dust, bacteria, and UV light. Further, the dome 102 is constructed from a translucent, UV-resistant material, that allows users to visually monitor the wound area without removing the reusable bandage device 100. Further, the dome 102 is designed such that the shape of the dome 102 ensures impact resistance, protecting the wound area from external pressure while maintaining structural integrity. In some embodiments, the dome 102 is configured to block ultraviolet light, thereby protecting the wound area from sun exposure. In some embodiments, the interior part of the dome 102 is structured to enclose the wound area without contacting a surface of the wound area, thereby allowing for undisturbed healing of the wound area. Further, the dome 102 comprises a solid and unperforated top surface to block ultraviolet (UV) light Further, the reusable bandage device 100 comprises a flange 104 that surrounds the dome 102. In some embodiments, the flange 104 is a flat and circular flange that extends outward to rest on the uninjured skin (also known as non-injured skin) around the wound area. The flange 104 provides a secure base for the reusable bandage device 100. In some embodiments, the flange 104 is formed with the base of dome 102 and extends outwards from the dome. In some other embodiments, the flange 104 extends around the base of the dome 102.

Further, the reusable bandage device 100 comprises slits 106 that are located on the flange 104. In some embodiments, the slits 106 may be located on either side of the flange 104, thereby providing a non-adhesive securing mechanism using a ribbon or strap, which may be threaded through the slits to hold the reusable bandage device 100 in place without relying on adhesive contact.

Figure 2:
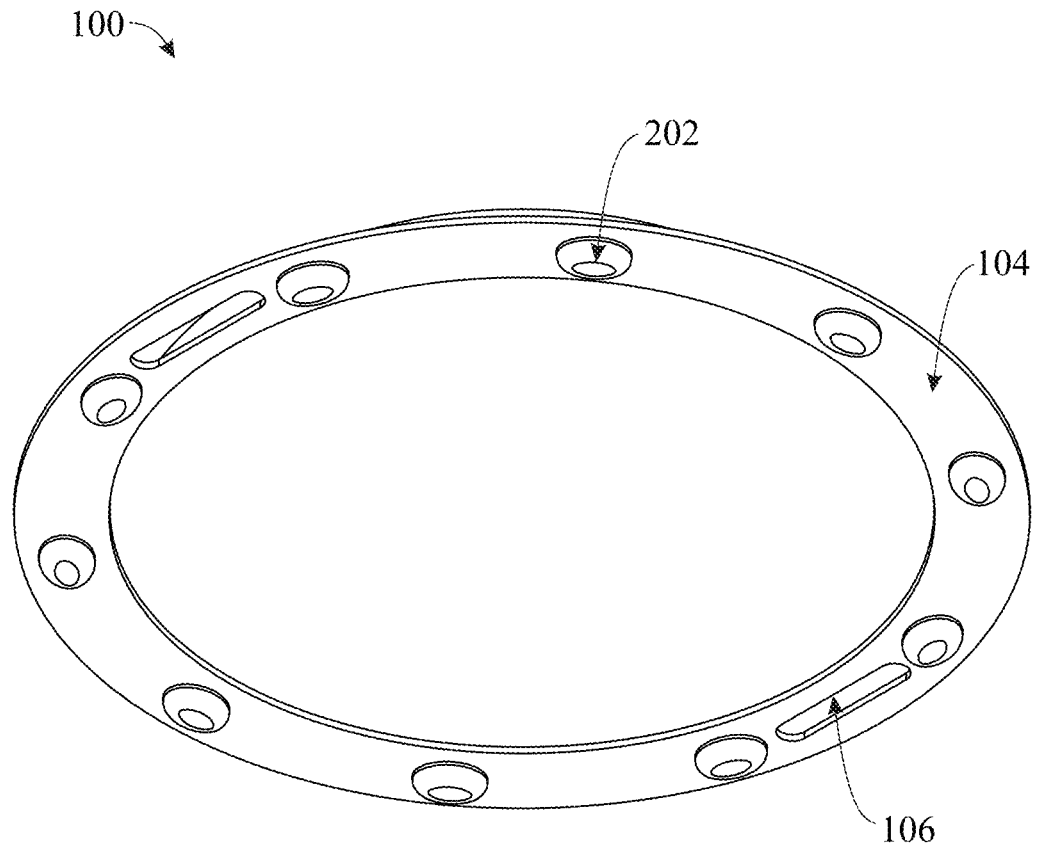
FIG. 2 illustrates a bottom view of the reusable bandage device in accordance with some embodiments of the present disclosure.

FIG. 2 illustrates a bottom view of the reusable bandage device 100 in accordance with some embodiments of the present disclosure. As shown in FIG. 2, the reusable bandage device 100 also comprises a plurality of protrusions 202 (also referred to as air channels) that are located on the underside of the flange 104. In some embodiments, the plurality of protrusions 202 is evenly spaced around the perimeter of the flange 104. The plurality of protrusions 202 creates a gap between the flange 104 and the skin of the person, thereby enabling airflow underneath the reusable bandage device 100.

In some embodiments, the plurality of protrusions 202 promotes ventilation and prevents moisture buildup around the wound area. By preventing the moisture buildup, the healing process may be accelerated by keeping the skin around the wound area dry. Further, in some embodiments, each of the plurality of protrusions 202 is flexible and/or detachable, thereby allowing for customizable airflow to the reusable bandage device 100. In some embodiments, each of the plurality of protrusions 202 is a raised structure under the flange 104. In some embodiments, the raised structure may be extended towards the dome 102. In some other embodiments, the raised structure may be extended towards the skin of the person. Further, each of the plurality of protrusions 202 is configured to allow airflow to the wound area while the dome 102 is securely positioned over the skin wound area.

Figure 3:
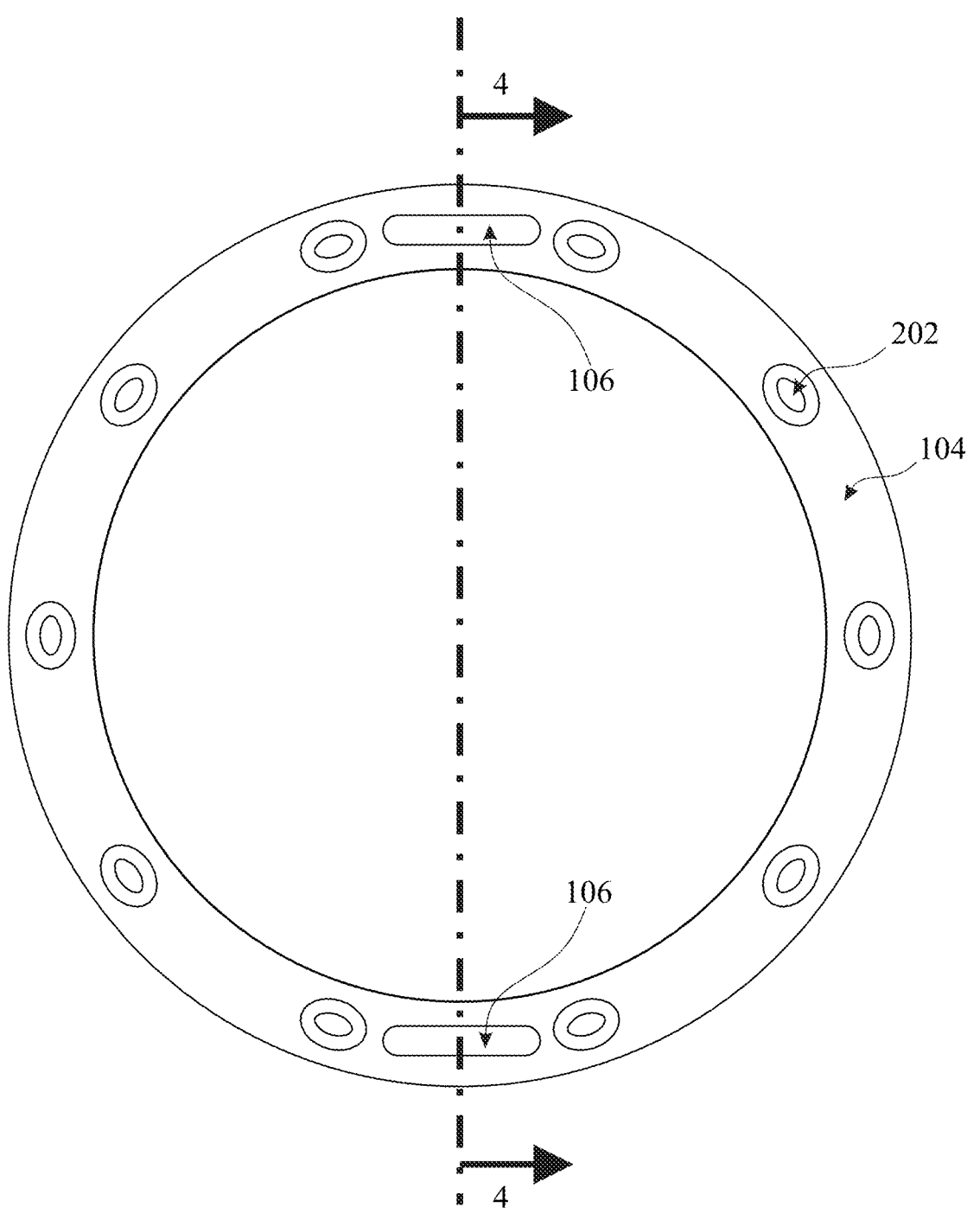
FIG. 3 illustrates a top-down view of the flange of the reusable bandage device in accordance with some embodiments of the present disclosure.

FIG. 3 illustrates a top-down view of the flange 104 of the reusable bandage device 100 in accordance with some embodiments of the present disclosure. As shown in FIG. 3, the plurality of protrusions 202 are arranged symmetrically around the circumference of the flange 104. The plurality of protrusions 202 are designed to provide ventilation by creating small gaps between the flange 104 and the skin of the person, promoting airflow to the wound area and preventing moisture buildup. In some embodiments, the plurality of protrusions 202 may vary in height or material flexibility, thereby allowing for customizable airflow and adaptability to different skin surfaces and wound conditions.

The slits 106 on the flange 104, positioned at the top and bottom, are intended for the insertion of a non-adhesive securing mechanism, such as a strap or ribbon, which may be used to fasten the reusable bandage device 100 without the need for adhesives. The non-adhesive securing mechanism is particularly useful for persons with sensitive skin or for areas of the body where adhesives are difficult to use. The reusable bandage device 100 remains securely in place while ensuring the wound is protected and well-ventilated. The symmetrical arrangement of protrusions 202 around the flange 104 helps to ensure the even distribution of the airflow and consistent skin ventilation around the wound area. In some embodiments, the size and the shape of each of the plurality of protrusions 202 is determined based on the size of the wound area and the healing stage. Further, in some other embodiments, the plurality of protrusions 202 within the flange 104 are arranged in a geometric pattern based on the size of the wound area.

Further, in some other embodiments, the height of each of the plurality of protrusions 202 is modified based on the wound area and the surrounding uninjured skin. Further, in some embodiments, at least one of the plurality of protrusions 202 may comprise one or more filter elements to prevent the entry of contaminants into the wound area.

Further, in some other embodiments, at least one of plurality of protrusions 202 may be perforated or hollow, thereby allowing air to pass through the protrusion itself in addition to the gap created by the plurality of air nodule's elevation.

Further, in some other embodiments, at least one of plurality of protrusions 202 may be designed to be detachable or interchangeable, thereby allowing users to customize the reusable bandage device 100 for different wound sizes or healing stages.

Figure 4:
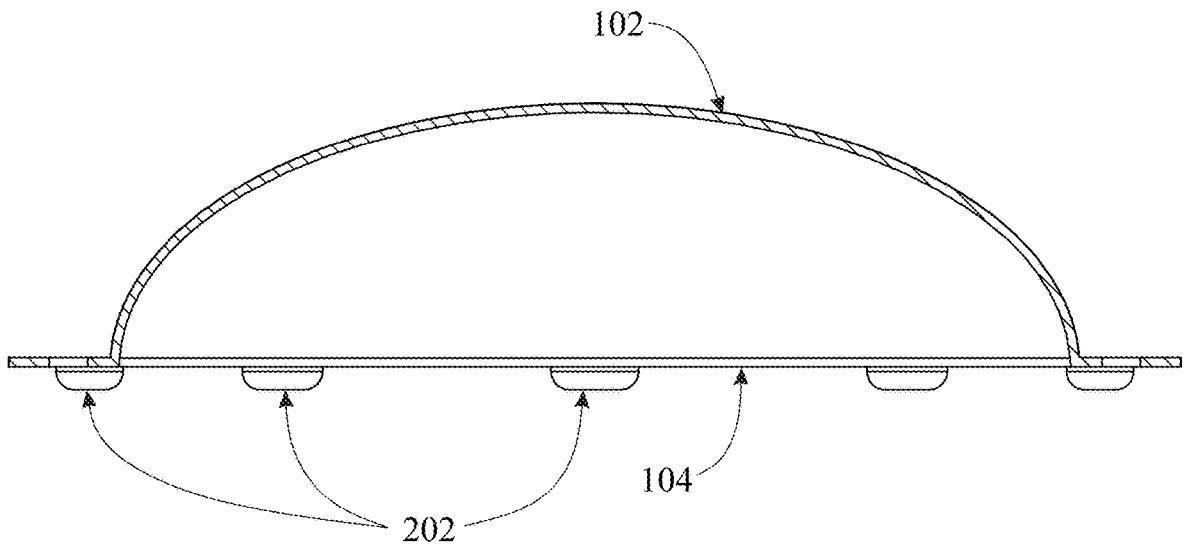
FIG. 4 illustrates a cross-sectional view of the reusable bandage device in accordance with some embodiments of the present disclosure.

FIG. 4 illustrates a cross-sectional view of the reusable bandage device, showcasing the structural relationship between the dome 102, the flange 104, and the protrusions 202. The dome 102 is depicted as a curved and semi-spherical structure that arches above the skin, which offers ample space for covering the wound area. The flange 104, which extends horizontally from the base of the dome 102, is designed to rest on the surrounding non-injured skin. Beneath the flange 104, several evenly spaced protrusions 202 are visible, functioning as protrusions to create a gap between the flange 104 and the skin. These protrusions 202 facilitate controlled airflow to the wound area, ensuring ventilation without direct contact.

Figure 5:
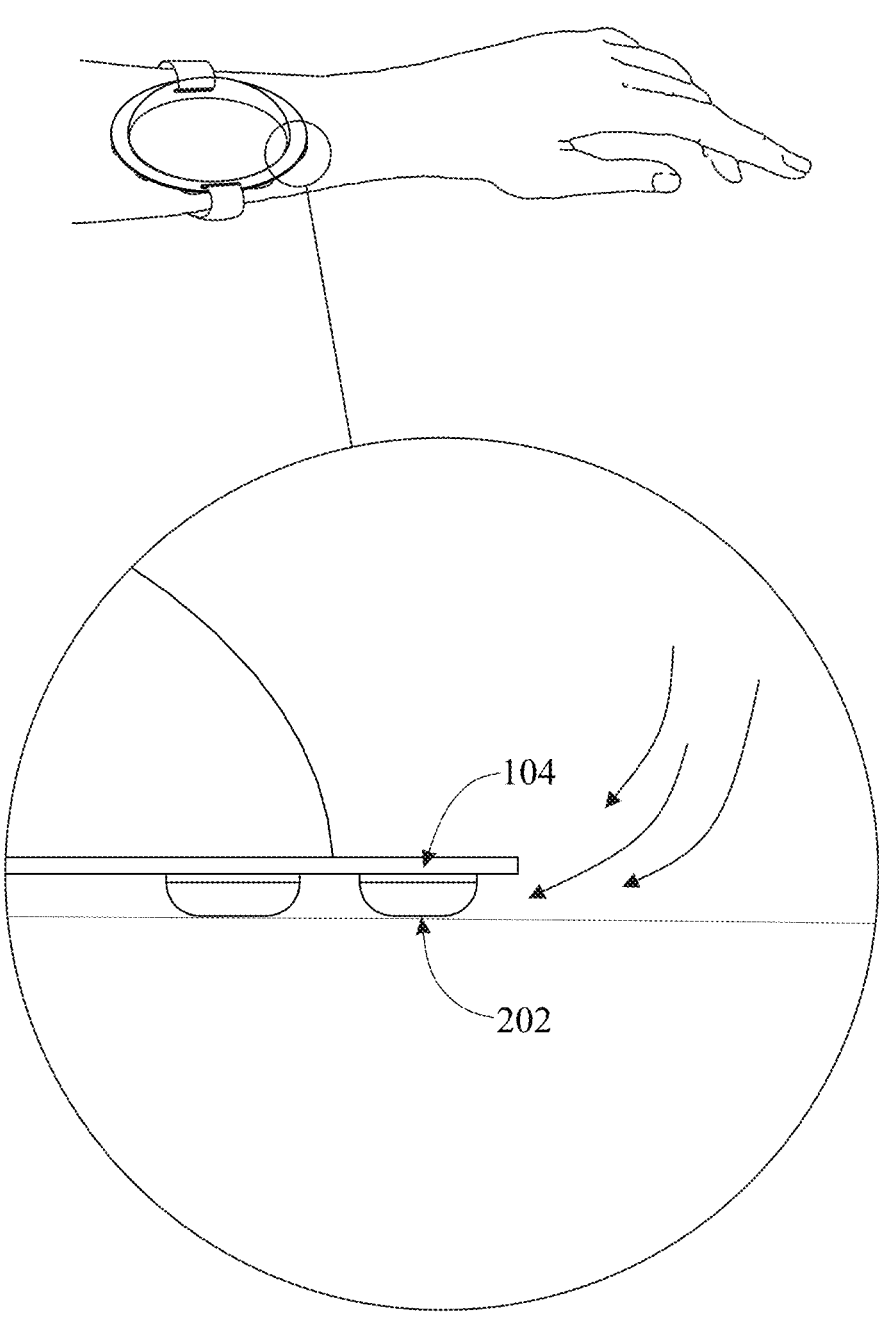
FIG. 5 illustrates the reusable bandage device when applied to a user in accordance with some embodiments of the present disclosure.

FIG. 5 illustrates the reusable bandage device 100 when applied to a user in accordance with some embodiments of the present disclosure. As shown in FIG. 5, the upper portion of the image shows the reusable bandage device 100 securely placed on a wrist or forearm of the user, illustrating how the reusable bandage device 100 fits around a wound site on an extremity without adhesive contact. Below, a magnified sectional view details the air circulation facilitated by the protrusions positioned beneath the flange 104. The dotted arrows indicate the flow of air between the skin surface and the flange 104, which is elevated by the protrusions 202. This gap ensures proper ventilation, allowing moisture to evaporate while maintaining protection over the wound area. Thus, by including the protrusions 202 on the reusable bandage device 100, the healing process is enhanced while keeping the reusable bandage device 100 securely in place without disrupting the skin beneath.

The above description of shown example implementations, including what is described in the Abstract, is not intended to be exhaustive or to limit the implementations to the precise forms disclosed. Although specific implementations of and examples are described herein for illustrative purposes, various equivalent modifications can be made without departing from the spirit and scope of the disclosure, as will be recognized by those skilled in the relevant art. Moreover, the various example implementations described herein may be combined to provide further implementations.

Since many modifications, variations, and changes in detail can be made to the described preferred embodiments of the disclosure, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A reusable bandage apparatus, comprising:
a dome configured to cover and enclose a skin wound, the dome comprising a continuous unperforated surface defining a physical barrier to prevent contact between the skin wound and external objects;
a flange extending around a base of the dome, wherein the flange is configured with a plurality of protrusions underneath the flange, whereby the plurality of protrusions is configured to rests on non-injured skin surrounding the skin wound; and
the plurality of protrusions located underneath the flange and arranged circumferentially around the flange on the underside thereof in a geometric pattern based on height, size, and shape of the skin wound, wherein the plurality of protrusions is configured to create a gap between each of the plurality of protrusions, and each of the plurality of protrusions raise a height of the flange above the non-injured skin.

2. The reusable bandage apparatus of claim 1, wherein the dome is a translucent, water-impermeable, optically transparent, and ultraviolet-resistant synthetic material.

3. The reusable bandage apparatus of claim 1, wherein each of the plurality of protrusions is a raised structure under the flange.

4. The reusable bandage apparatus of claim 1, wherein each of the plurality of protrusions lifts the flange above the non-injured skin while the dome is securely positioned over the skin wound.

5. The reusable bandage apparatus of claim 1, wherein the plurality of protrusions are adjacently spaced from touching each other whereby each of the plurality of protrusions underneath the flange are spaced apart along a perimeter of the flange.

6. The reusable bandage apparatus of claim 1, wherein each of the plurality of protrusions are detachably secured underneath the flange to permit replacement or height adjustment.

7. The reusable bandage apparatus of claim 1, wherein the dome is configured to block ultraviolet light from touching the skin wound enclosed inside the dome.

8. The reusable bandage apparatus of claim 1, wherein the dome comprises a transparent material that enables visual inspection of the skin wound without removing the reusable bandage apparatus.

9. The reusable bandage apparatus of claim 1, further comprising:
slits through the flange for insertion of a ribbon tape, wherein the ribbon tape is configured to secure the bandage apparatus around an extremity without adhesive, and
wherein the plurality of protrusions are configured to maintain airflow for the skin wound independent of the tightness of fit of the ribbon tape.

10. The reusable bandage apparatus of claim 1, wherein an interior part of the dome is structured to enclose the skin wound without contacting the surface of the skin wound.

11. The reusable bandage apparatus of claim 1, wherein the unperforated surface is configured to block ultraviolet (UV) light from penetrating through the dome.

12. The reusable bandage apparatus of claim 1, wherein a height of each of the plurality of protrusions is adjustable based on the height and size of the skin wound enclosed by the reusable bandage apparatus.

13. A wound care apparatus, comprising:
a reusable dome configured to cover and enclose a wound area, the dome comprising a continuous unperforated surface constructed from an optically transparent, ultraviolet-resistant material defining a physical barrier to prevent contact between the wound area and external objects;
a flange extending around a base of the dome, the flange configured with a plurality of protrusions underneath; and
the plurality of protrusions located underneath the flange and configured to lift the flange above the skin, wherein the plurality of protrusions are arranged circumferentially around the flange in a geometric pattern based on height, size, and shape of the skin wound, where the plurality of protrusions are configured to create a gap between each of the plurality of protrusions, and each of the plurality of protrusions raise a height of the flange above the non-injured skin.

14. The wound care apparatus of claim 13, wherein the plurality of protrusions are arranged, evenly spaced, and adjacently spaced from each other allowing the gap between each of the plurality of protrusions.

15. The wound care apparatus of claim 13, wherein a height of each of the plurality of protrusions is modified based on the wound area and the surrounding uninjured skin.

16. The wound care apparatus of claim 13, wherein at least one of the plurality of protrusions comprises one or more filter elements to prevent entry of contaminants to the wound area.

17. The wound care apparatus of claim 13, wherein the dome is provided with an adjustable securing mechanism comprising one or more attachment elements coupled to the flange for securing the wound care apparatus to surrounding body parts without usage of adhesives.

18. The wound care apparatus of claim 17, wherein the securing mechanism comprises a non-adhesive and elastic strap threaded through slits in the flange for adjustable and secure attachment around the wound area.

19. The wound care apparatus of claim 13, wherein each of the plurality of protrusions are detachable from the flange.

20. The wound care apparatus of claim 13, wherein a size and a shape of each protrusion are based on a size of the wound area, and a healing stage.

\* \* \* \* \*